United States Patent
Kleinschmidt et al.

(10) Patent No.: US 7,629,322 B2
(45) Date of Patent: Dec. 8, 2009

(54) AAV VECTOR FOR GENE THERAPY

(76) Inventors: Jürgon Kleinschmidt, Weihwiescnweg 5, 69245 Bammenthal (DE); Oliver Müller, Am Kirchberg 15, 69221 Dossenheim (DE)

( * ) Notice: Subject to any disclaimer, the term of this patent is extended or adjusted under 35 U.S.C. 154(b) by 0 days.

(21) Appl. No.: 10/560,268

(22) PCT Filed: Jun. 9, 2004

(86) PCT No.: PCT/EP2004/006222

§ 371 (c)(1),
(2), (4) Date: Jun. 14, 2006

(87) PCT Pub. No.: WO2004/111248

PCT Pub. Date: Dec. 23, 2004

(65) Prior Publication Data

US 2007/0036757 A1 Feb. 15, 2007

(30) Foreign Application Priority Data

Jun. 11, 2003 (EP) .................................. 03013169

(51) Int. Cl.
*A61K 31/70* (2006.01)
*A61K 48/00* (2006.01)
*C12N 15/861* (2006.01)

(52) U.S. Cl. .................. 514/44; 424/93.2; 435/456

(58) Field of Classification Search ........................ None
See application file for complete search history.

(56) References Cited

U.S. PATENT DOCUMENTS 6,162,796 A * 12/2000 Kaplitt et al. .................. 514/44
6,962,815 B2 * 11/2005 Bartlett ........................ 435/455
2006/0088936 A1 * 4/2006 Warrington et al. ......... 435/456

FOREIGN PATENT DOCUMENTS

WO WO 2004/027019 A3 4/2004

OTHER PUBLICATIONS

Grifman M, Trepel M, Speece P, Gilbert LB, Arap W, Pasqualini R, and Weitzman MD. Incorporation of Tumor-Targeting Petides into Recombinant Adeno-associated Virus Capsids. Molecular Therapy 3(6): 964-975. Jun. 2001.*
Verma et al (Nat. 1997 Sep; 389:239-242).*
Eck et al. (Phar Basis Ther 1995; 77-101).*
Xie et al. PNAS 2002; 99(16):10405-10410.*
Wu Xiao (PhD Dissertation 2002, University of Florida).*
Kern A. et al: "Identification of a Heparin-Binding Motif on Adeno-Associated Virus Type 2 Capsids", Journal of Virology, Oct. 2003, pp. 11072-11081.
Opie S. R. et al: "Identification of Amino Acid Residues in the Capsid Proteins of Adeno-Associated Virus Type 2 That Contribute to Heparan Sulfate Proteoglycan Binding", Journal of Virology, Jun. 2003, pp. 6995-7006.

* cited by examiner

*Primary Examiner*—Janet L Epps-Smith
*Assistant Examiner*—Scott Long
(74) *Attorney, Agent, or Firm*—Howrey LLP; Viola T. Kung

(57) ABSTRACT

Described are recombinant AAV vectors characterized in that they carry capsid protein modification(s) resulting in a reduced or eliminated heparin binding function. The AAV vectors of the present invention are particularly suitable for gene therapy by systemic application, since (a) transduction of the liver is eliminated or at least drastically reduced and (b) the transduction efficiency of non-hepatic tissues is increased.

4 Claims, 7 Drawing Sheets

Fig. 1

```
421 HSSYAHSQSL DRLMNPLIDQ YLYYLSRTNT PSGTTTQSRL QFSQAGASDIRDQSRNWLPG
        #13,14 #15,16              #10       #11       #1    #12
481 PCYRQQRVSK TSADNNNSEY SWTGATKYHL NGRDSLVNPG PAMASHKDDE HKFFPQSGVL
        #21,22 #2              #3 #23           #24,25         #18           #19    #20
541 IFGKQGSEKT NVDIEKVMIT DEEERTTNP VATEQYDSVS INLQRGNRQA AIAEDVNTQGV
                              #34       #26-28 #29-32 #4 #35 #5
601 LPGMVWQDRD VYLQGPIWAK
         #33
```

C liver heart lung kidney

AAV VECTOR FOR GENE THERAPY

This application is a National Stage of International Application PCT/EP2004/006222, filed Jun. 9, 2004, published Dec. 23, 2004, under PCT Article 21(2) in English; which claims the priority of EP 03013169.2, filed Jun. 11, 2003.

The present invention relates to a recombinant AAV vector characterized in that it carries capsid protein modification(s) resulting in a reduced or eliminated heparin binding function. The AAV vector of the present invention is particularly suitable for gene therapy by systemic application, since (a) transduction of the liver is eliminated or at least drastically reduced and (b) the transduction efficiency of non-hepatic tissues is increased.

Safety and efficacy of human gene therapy continue to be the subject of considerable debate. Problems of current vectors include unintended transduction of certain tissues, adverse immune reactions, and lack of efficient transduction of the tissue of interest. The most commonly used gene transfer systems to date are derivatives of viruses, e.g. adeno-associated virus type 2 (AAV-2). Unfortunately, the systemic or intraperitoneal application of such viral vectors for gene therapy results in the preferred accumulation of the viruses within the liver. This is due to the fact, that attachment of a virus to the host cell requires a specific interaction of the virus shell with cellular receptor molecules. These permit uptake and thus intracellular processing of the virus to successfully infect the cell. For adeno-associated virus type 2 (AAV-2), a member of the parvovirus family containing a non-enveloped icosahedral capsid, heparan sulfate proteoglycan of liver cells has been shown to act as a primary receptor. However, the contribution of additional receptor(s) has been postulated because AAV-2 binding to cells and recombinant AAV-2 (rAAV-2) transduction did not quantitatively correlate with the amount of heparan sulfate on the cell surface of different cell types tested. After binding to the cell surface, AAV-2 is thought to engage a secondary receptor which mediates cell entry. To date, αVβ5 integrin and human fibroblast growth factor receptor 1 (FGFR1) have been proposed, but the involvement of other molecules has also been suggested.

Heparan sulfate glucosamino-glycans (HSGAG) are complex polysaccharides with high structural diversity. They consist of repeating disaccharide units each composed of a glucuronic acid or iduronic acid linked to a glucosamine. The immense structural diversity of HSGAG's arises from the modification of individual disaccharide units within the oligosaccharide. This enables these molecules to interact with a wide variety of proteins such as growth factors, chemokines, morphogens, enzymes, matrix proteins, lipoproteins and antimicrobial peptides which are involved in diverse biological processes such as morphogenesis, tissue repair, energy balance, host defense, cell adhesion, proliferation and growth factor signalling. Numerous viruses, e.g. HSV-1 and 2, human immunodeficiency virus, respiratory syncytial virus, dengue virus, pseudorabies virus, foot and mouth disease virus, vaccinia virus, Sindbis virus, several papillomaviuses, cytomegalovirus, AAV-2 and AAV-3 and others bind to HSGAGs.

The HSGAG chains are assembled while attached to a proteoglycan core protein. So far, three major protein families have been characterised: the membrane spanning syndecans, the glycosylphosphatidylinositol-linked glypicans and the basement membrane proteoglycans perlecan and agrin. The sequence of the HSGAGs does not correlate with the proteins to which they are bound but rather resembles the cell type in which the HSGAG has been synthesized. HSGAGs interact with proteins mainly via electrostatic interactions of basic amino acids with the negatively charged sulfo- and carboxyl-groups of the HSGAG chain. However, hydrogen bond formation and to a smaller extent hydrophobic interactions can also contribute to this type of interaction. Heparin-binding domains of heparin-binding proteins have been shown to contain consensus sequence motifs such as XBBXB and XBBBXXBX (where B is a basic amino acid exposed on one side and X is a neutral or hydrophobic amino acid directed towards the protein interior). By analysing the available experimentally determined heparin-protein complexes it became obvious that the spatial orientation of basic residues, rather than sequence proximity is an important factor in determining heparin binding affinity. Such binding domains are usually located at the protein surface and form a flat pocket of positive charge.

The undesired uptake of AAV-2 based vectors by the liver might lead to severe side effects, e.g., drastically reduced levels of viruses which no longer allow efficient transduction of the desired target tissue. So far, this problem has been tried to overcome by replacing the systemic or intraperitoneal injection (a) by direct injection of a solution containing the viral vector or (b) by increasing the dosis. By using a tissue specific promoter expression of the foreign gene in the liver is supressed. However, the approaches used so far exhibit a variety of severe disadvantages, e.g., (a) systemic or intraperitoneal application is not reasonable, (b) fatal incidents after increase of dosis have been described, (c) the use of a tissue specific promoter for avoiding gene expression does not solve the problem of decrease of the level of viruses due to their accumulation within the liver.

Therefore, it is the object of the present invention to provide AAV vectors which do not exhibit the disadvantages of the AAV vectors of the prior art, i.e., which show reduced accumulation within the liver resulting in (a) increased safety and (b) higher transfection rates of the target tissue.

According to the invention this is achieved by the subject matters defined in the claims. The capsid of AAV-2 is composed of three overlapping capsid proteins (VP1; VP2, VP3) containing a unique VP1 N-terminus, a VP1/VP2 common portion and a portion which is common to VP1, VP2 and VP3 (Srivastava et al. (1983) J. Virol. 45:555-64; Trempe et al. (1988), J. Virol. 62:3356-63; Cassinotti et al. (1988) Virology. 167:176-84). To date, the VP protein domains involved in binding to heparin have not been studied in detail. Several short basic sequences located in the N-terminal portion of VP1 and VP2 have been proposed as possible candidates for heparin binding. However, capsids mutated in these amino acids and capsids composed only of VP3 molecules still showed binding to heparin. The present invention is based on the applicant's identification of a capsid protein domain and corresponding amino acid residues involved in heparin binding. Mutational analysis of AAV-2 capsid proteins VP1, VP2 and VP3, respectively showed that a group of basic amino acids (arginines 484, 487, 585, 588 and lysine 532; numbering according to the numbering based on VP1 protein id AAC03780.1 NCBI accession No. AF043303) contributes to heparin and HeLa cell binding. These amino acids are positioned in three clusters on the threefold spikes of the AAV-2 capsid. According to the recently resolved atomic structure for AAV-2, arginines 484, 487 and lysine 532 on one site and arginines 585 and 588 on the other site belong to different capsid protein subunits. This suggests that the formation of the heparin-binding motifs depends on the correct assembly of VP trimers or even of capsids. In contrast, arginine 475 which also strongly reduced heparin binding as well as viral infectivity upon mutation to alanine is located inside the capsid structure at the border of adjacent VP subunits and most probably influences heparin binding indirectly by disturbing correct subunit assembly. Computer simulation of heparin docking to the AAV-2 capsid suggests that heparin associates with the three basic clusters along a channel-like cavity flanked by the basic amino acids. With few exceptions, mutant infectivities correlated with their heparin- and cell-binding properties. Tissue distribution in mice of a recombinant AAV-2 mutated in R484 and R585 showed a highly reduced infection of liver compared to wt rAAV but continued to infect heart tissue. These results suggest that although heparin-binding influences infectivity of AAV-2, it seems not to be necessary.

Accordingly, the AAV vectors of the invention have substantial advantages over the vectors of the prior art and are particularly suitable for gene therapy by systemic application, since (a) transduction of the liver is eliminated or at least drastically reduced and (b) the transduction efficiency of non-hepatic tissues, e.g., heart muscle tissue, is, unexpectedly, increased. Accordingly, side effects due to the accumulation of AAV within the liver can be avoided and the vector doses required for efficient transduction can be reduced.

FIG. 2: Influence of Mutations of Arginines 585 and 588 on Infectivity, Cell Binding and Heparin-Binding of AAV-2

Virus stocks were produced by transfection of wt or mutated AAV-2 genomic plasmids into 293T cells and superinfection with adenovirus (MOI=10).

(A) Infectious titers were determined as described in Example 1. Capsid titers and genomic titers were not influenced by the mutations (data not shown), implying that they did not affect capsid assembly or genome encapsidation.

(B) Virus-cell binding was measured on HeLa cells using mAb A20 for detection of cell bound virus (Wobus et al. (2000), J. Virol. 74:9281-93).

(C) Heparin binding was assayed by chromatography of virus preparations (freeze-thaw lysates) on heparin agarose and quantitation of applied, flow through and salt eluted virus carried out using the A20 capsid ELISA. The amount of applied virus was set to 100%. Error bars indicate standard deviations of at least three independent experiments.

FIG. 3: Analysis of Distant Amino Acids for their Contribution to Heparin Binding Virus stocks were produced by transfection of wt or mutated AAV-2 genomic plasmids into 293T cells and superinfection with adenovirus (MOI=10).

(A) Infectious titers were determined as described in Example 1. Capsid titers and genomic titers were riot influenced by the mutations (data not shown), implying that they did not affect capsid assembly and genome encapsidation.

(B) Virus-cell binding was measured on HeLa cells using mAb A20 for detection of cell bound virus (Wobus et al. (2000), J. Virol. 74:9281-93).

(C) Heparin binding was assayed by chromatography of the virus preparations (freeze-thaw lysates) on heparin agarose and quantitation of applied, flow through and salt eluted virus carried out using the A20 capsid ELISA. The amount of applied virus was set to 100%. Error bars indicate standard deviations of at least three independent experiments.

FIG. 4: Further Loop IV Basic Amino Acids Involved in AAV-2 Binding to Heparin Indicated amino acids were mutated and virus stocks obtained from freeze-thaw lysates of 293T cells transfected of wt or mutated AAV-2 genomic plasmids and superinfection with adenovirus-5 (MOI=10). Virus stocks were analysed for infectivity, cell binding and heparin binding.

(A) Infectious titer was measured as described in Example 1.

(B) Virus-cell binding was measured on HeLa cells using mAb A20 for detection of cell bound virus (Wobus et al. (2000), J. Virol. 74:9281-93).

(C) Heparin binding was assayed by chromatography of the virus preparations (freeze-thaw lysates) on heparin agarose and quantitation of applied, flow through and salt eluted virus carried out using the A20 ELISA. The amount of applied virus was set to 100%. Error bars indicate the standard deviation of at least three independent experiments.

FIG. 5: In vivo Distribution of wt and Mutant R484E/R585E rAAV in Mouse Tissues Luciferase activities in different organs after intravenous injections of $10^{11}$ recombinant AAV with wild-type capsids (AAVwt) (A) and AAVs with mutation of heparin binding sites (R484E; R585E) (B). Luciferase activities are depicted in relative light units (RLU) per mg protein. (C) Detection of luciferase gene transfer by PCR in selected organs three weeks after intravenous injection of $10^{11}$ genomic particles of AAV(R484E; R585E) and AAVwt in representative organs. PCR amplification of genomic DNA extracted from liver tissue of different mice using luciferase and β-actin primers showed that the 677 bp luciferase band is faint or absent in liver tissue of mice injected with AAV(R484E; R585E), but clearly visible in mice injected with wild-type AAV. PCR amplification of tissue samples from heart, lung and kidney did not reveal any difference in expression.

FIG. 6: Localisation of Amino Acids Involved in Heparin Binding on the AAV-2 Capsid Surface (A) The amino acids involved in heparin binding R585 (orange), R588 (red), R484 (purple), R487 (green), K532 (blue), 475 (yellow) are grouped in three clusters at the threefold spike region of the capsid. The inset shows a VP trimer which forms the threefold spikes.

(B) A cross-section through a VP-trimer visualises the surface exposure of the basic clusters at the inner shoulder of the threefold spikes and along a channel-like structure between the three fold spikes. R475 is burried in the capsid wall (at the border of two subunits, not shown) and likely affects heparin binding indirectly when it is mutated to alanine. The unmarked residues are derived from the second-hand third spikes.

(C) Two different protein, subunits (indicated in red, blue and green) contribute to the formation of a basic heparin-binding cluster.

FIG. 7: Computer Simulation of Heparin Docking to, the AAV-2 Capsid Surface

The docking simulation was performed as described in Example 1. The blue orbitals show the heparin hexamer. Amino, acids coming into proximity to the heparin molecule which might permit electrostatic or hydrogen bond interactions are indicated. Letters A, B, and C indicate the three different VP subunits involved in heparin binding.

The present invention relates to an AAV vector characterized in that it carries at least one mutation resulting in a heparin-binding motif of a capsid protein (VP1, VP2 and VP3, respectively) being located within aa positions 470 to 592 (according to the numbering based on VP1 protein id

AAC03780.1 NCBI accession No. AF043303) showing a reduced or eliminated heparin binding function.

The person skilled in the art knows how to modify and propagate AAV. For example, AAV-2 can be propagated both as lytic virus and as a provirus. For lytic growth AAV requires co-infection with a helper virus. Either adenovirus or herpes simplex can supply helper function. Without helper, there is no evidence of AAV-specific replication or gene expression. When no helper is available, AAV can persist as an integrated provirus. Integration apparently involves recombination between AAV termini and host sequences and most of the AAV sequences remain intact in the provirus. The ability of AAV to integrate into host DNA is apparently an inherent strategy for insuring the survival of AAV sequences in the absence of the helper virus. When cells carrying an AAV provirus are subsequently superinfected with a helper, the integrated AAV genome is rescued and a productive lytic cycle occurs. AAV sequences cloned into prokaryotic plasmids are infectious. For example, when wild type AAV/pBR322 plasmid is transfected into human cells in the presence of adenovirus, the AAV sequences are rescued from the plasmid and a normal AAV lytic cycle esues. This renders the possibility to modify the AAV sequences in the recombinant plasmid and, then, to grow a viral stock of the mutant by transfecting the plasmid into human cells. The construction of rAAV vectors carrying particular modifications and the production of rAAV particles, e.g., with modified capsids, is described, e.g., in Shi et al. (2001), Human Gene Therapy 12:1697-1711; Rabinowitz et al. (1999), Virology 265:274-285; Nicklin et al. (2001), Molecular Therapy 4:174-181; Wu et al. (2000), J. Virology 74:8635-8647; and Grifman et al. (2001), Molecular Therapy 3:964-974. Thus, based on is background knowledge and the information provided herein as regard the location/structure of the domain of the AAV capsid responsible for preferred transduction of liver cells, the person skilled in the art can construct recombinant AAV vectors of the present invention which show a reduced or eliminated heparin binding function. Such modification can be achieved by replacing amino acid residues located, at critical positions, e.g., the positions described in the examples, by other amino acid residues. Alternatively, amino acid residues at critical positions can be eliminated or one or more amino acid residues can be inserted thereby distorting the spatial structure of the heparin binding domain in such a way that heparin binding is eliminated or at least weakened.

In a preferred embodiment, the AAV vector of the present invention contains (a) mutation(s) resulting in an amino acid substitution of the capsid protein at aa position: (a) arginine 475; (b) arginine 484; (c) arginine 487; (d) lysine 527; (e) lysine 532; (f) arginine 585; and/or (g) arginine 588. Preferably, said amino acid substitution is a non-conservative amino acid substitution.

In a more preferred embodiment, the AAV vector of the present invention is characterized by at least one of the following amino acid substitutions: (a) R475A; (b) R484A or R484E; (c) R487A or R487E; (d) K527A; (e) K532A; (f) R585E; and/or (g) R588E.

Particularly preferred is an AAV vector, wherein the capsid protein is characterized by the amino acid substitutions R484E and/or 585E.

AAV vectors suitable for use in the present invention are based on AAV2 or AAV3, with AAV-2 being preferred.

The present invention also relates to a pharmaceutical composition containing an AAV7 vector or AAV particle of the present invention. The pharmaceutical composition containing an AAV vector or particle of the invention, preferably, contains a pharmaceutically acceptable excipient, diluent or carrier. Examples of suitable pharmaceutical carriers etc. are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the suitable compositions may be effected by different ways, e.g. by intravenous, intraperitoneal, subcutaneous, intramuscular, topical or intradermal administration. The route of administration, of course, depends, inter alia, on the kind of vector contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind and stage of infection or disease, general health and other drugs being administered concurrently.

Finally, the present invention relates to the use of an AAV vector or AAV particle of the invention for gene therapy of non-hepatic tissues such as heart muscle tissue.

The following Examples illustrate the invention.

EXAMPLE 1

Materials and Methods (A) Cell Culture 293T and HeLa cells were maintained in Dulbecco's modified Eagle's medium (DMEM) supplemented with 10% heat-inactivated fetal calf serum (FCS), 2 mM L-glutamine, 100 U/ml penicillin and 1 mg/ml streptomycin at 37° C. in 5% $CO_2$.

(B) Transfection and Preparation of Virus Supernatants 293T cells were plated at $1.5 \times 10^6$ cells per 10 ml of DMEM medium with 10% FCS per 10 cm Petri dish 1 day prior to transfection. Transfections were carried out using 12 µg of DNA per dish according to the method of Chen and Okayama ((1988), Biotechniques 6:632-8). 16-18 h post-transfection, the medium was replaced by 10 ml medium containing adenovirus-5 (Ad5) (m.o.i. (multiplicity of infection) of 50). The cultures were incubated for 2 days at 37° C. and 5% $CO_2$. Cells were harvested in 10 ml medium and lysed by three rounds of freeze-thawing (−80° C. and 37° C.) to release the produced virus. Cell debris was removed by centrifugation at 400×g for 10 min. Prior to cell lysis an aliquot of 300 µl of the harvested cells was taken, washed once with phosphate-buffered saline (PBS) and was denatured by heating at 100° C. for 5 min in presence of SDS sample buffer. After sonification, the samples were analysed by western blotting.

(C) Determination of Viral Titers

Quantitation of AAV-2 capsid titers was carried out by an ELISA according to Grimm et al. (199 g), Gene Ther. 6:1322-30, using pre-coated plates supplied by Progen GmbH (Heidelberg, Germany). Infectious and genomic titers were determined as described previously (King et al. (2001), Embo J. 20:3282-91). Random-primed $^{32}$P-labelled probes were generated from a rep fragment (XhoI/BamHI) of plasmid pBSΔTR-18 (Weger et al. (1997), J. Virol. 71:8437-47).

(D) Plasmids and Mutagenesis

The DTAV2-0 plasmid (Heilbronn et al. (1990), J. Virol. 64:3012-8) contains the entire AAV-2 genome from pAV-2 (Laughlin et al. (1983) Gene 23:65-73) including both inverted terminal repeats cloned into the BamHI site of pbluescript II. The pJ407 plasmid which was used as the template for the site-directed mutagenesis reactions contains the BamHI-NotI fragment of the AAV-2 genome from pTAV2-0 cloned into pUC131. Mutagenesis was performed by using the Stratagene QuikChange Site-Directed Mutagenesis Kit (Stratagene, Amsterdam, Netherlands) according to the manufacturer's protocol. For each mutant, two complementary PCR Primers were designed which contained the sequence of the substitution or deletion, respectively, flanked by 15 to 20 homologous base pairs on each side of the mutation. Mutant plasmids were identified by DNA sequencing. The BsiWI-XcmI (respectively XcmI-EcoNI) fragment containing the mutation was then subcloned into the pTAV2-0 backbone. The complete fragment was sequenced to check for additional PCR mutations. Deletion mutant #6 was constructed by inserting a double stranded oligo (5-CGTTAAC-CCAGGCATGGTCTGGGC-3', SEQ ID NO: 1,5'-CCCA-GACCATGCCTGGGTTAACGCATG-3'. SEQ ID NO: 2) providing an additional XcmI site into the SphI site of mutant #29. The resultant plasmid was digested by XcmI and religated.

(E) Western Blot Analysis

Western blot analysis and antibodies 303.9 and B1 were described previously (Wistuba et al. (1995), J. Virol. 69:5311-9). Peroxidase-coupled secondary antibodies and the enhanced chemiluminescence kit (NEN, Cologne, Germany) were used according to standard methods.

(F) Cell-Binding Assay

Cell binding was measured essentially as described (Wobus et al. (2000), J. Virol. 74:9281-93). Briefly, HeLa cells were plated out at $10^4$ cells/well on microtiter plates (Nunc, Wiesbaden, Germany) in 100 µl medium 1 day prior infection. Virus supernatants were diluted to $1 \times 10^9$-$1 \times 10^{10}$ capsids/well in pre-cooled medium without FCS. The cells were incubated with 50 µl/well of the dilutions in triplicate for 60 min at 4° C. After washing with 200 µl/well of cooled phosphate-buffered saline, the cells were fixated with 100 µl/well methanol cooled to −20° C. for 15 minutes and dried at room temperature over night. After washing three times with PBS containing 0.05% Tween-20 (wash buffer), the cells were blocked with 200 µl/well of PBS containing 0.2% casein and 0.05% Tween-20 (blocking buffer) for 2 h at 37° C. The blocking buffer was removed and replaced by blocking buffer containing 100 ng/well of biotinylated A20 antibody (Grimm et al. (1999), Gene Ther. 6:1322-30; Grimm and Kleinschmidt (1999), Hum. Gene Ther. 10:2445-50) and incubated for 90 minutes at room temperature. Unbound A20 was removed by washing three times with wash buffer. Then the cells were incubated with 100 µl/well of streptavidin-coupled peroxidase diluted to a final concentration of 0.8 µg/ml in blocking buffer for 1 h at room temperature. After washing three times with wash buffer, the plates were incubated with 100 µl tetramethylbencidine substrate (Devitron, Castrop-Rauxel, Germany). The reaction was stopped by adding 50 µl of 1 M $H_2SO_4$ to each well. Absorption at 450 nm was measured using an ELISA Reader (MG, Ebersberg, Germany). Cell-binding was expressed as percentage of adsorption measured with the AAV-2 wt virus stock using the same capsid number.

(G) Heparin-Binding Assay

A 1 ml heparin column (Sigma, Munich, Germany) pre-equilibrated with 20 ml of PBS containing 1 mM $MgCl_2$ and 2.5 mM KCl (PBS-MK) was loaded with 5 ml of virus supernatant. The column was washed with 2×5 ml of PBS-MK and eluted with 2×5 ml of PBS containing 1 M NaCl. The flow-through, wash and eluate fractions were analysed with the A20 capsid ELISA as described above. Values are given as percentage of capsids applied to the column.

(H) Generation of AAV Vectors and Determination of Titers

For generation of rAAV-vectors carrying a luciferase reporter gene, the capsid region carrying both mutations (R484E and R585E) was excised XcmI/BsiWI from plasmid J407R-585-E-1 and inserted into pBSΔTR18, providing rep- and cap-genes without ITRs (Heilbronn et al. (1990), Journal of Virology 64:3012-8). The helper plasmid pDGΔHS was obtained by excision of the mutated cap-gene from the modified pBSΔTR18 with SwaI/ClaI and insertion into the corresponding position of pDGΔVP (Dubielzig et al. (1999), Journal of Virology 73:8989-98). pUFCMV-Luc is derivative of pUF3 (Zolotukhin et al. (1996), Journal of Virology 70:4646-54) harboring the firefly luciferase sequence from pGL3-basic (Promega, Mannheim, Germany) inserted into the HindIII and blunted 3' XhoI site. For production of AAV with modified or wild-type capsids, 293T cells were transfected with pUFCMV-Luc and pDGΔHS or pDG, respectively, using calcium phosphate precipitation (Hauswirth et al. (2000), Methods in Enzymology 316:743-61). After 72 h cells were harvested and viruses were purified using iodixanol gradients (Hauswirth et al. (2000), Methods in Enzymology 316:743-61). The AAV genomic, capsid, and replicative titers were determined as described previously (Grimm et al. (1999), Gene Therapy 6:1322-1330). For heparin binding, $10^9$-$10^{10}$ particles in PBS containing 1 mM $MgCl_2$ and 2.5 mM KCl (PBS-MK) were bound to 1 ml heparin agarose (Sigma, St. Louis, Mo.), washed twice with 5 ml PBS-MK, and eluted twice with 2 ml PBS containing 1M NaCl. Fractions were collected and analyzed with the A20-ELISA (Grimm et al. (1999), Gene Therapy 6-1322-1330).

(J) In Vivo Characterization of Vectors

All procedures involving the use and care of animals were performed according to Guide for the Care and Use of Laboratory Animals published by the US National Institutes of Health (NIH Publication No. 85-23, revised 1996) and the German animal protection code. Female immunocompetent NMRI mice (6-8 weeks of age) were purchased by the German branch of Charles River Laboratories (Wilmington, Mass.). Six mice per group were injected intravenously via the tail vein with concentrated vector from two independent preparations using a 30-gauge needle. After three weeks mice were sacrificed and representative organs (heart, lung, liver, kidney) were harvested and frozen in liquid nitrogen.

(K) Detection of AAV Genomes by PCR

Genomic DNA was extracted from organs using the Qiamp Tissue Kit (Qiagen, Hilden, Germany). 800 ng genomic DNA was used for PCR-amplification (40 cycles) of a 677 bp fragment of the luciferase gene using the primers 5'-GACGC-CAAAAACATAAAGAAAG-3', SEQ ID NO: 3, and 5'-CCAAAAATAGGATCTCTGGC-3', SEQ ID NO: 4, under standard conditions. Integrity of DNA was determined by amplifying a 492 bp region of the murine β-actin gene using the primers 5'-ATGTTTGAGACCTTCAACAC-3', SEQ ID NO: 5, and 5'-AACGTCACACTTCATGATGG-3', SEQ ID NO: 6. PCR products were analyzed by gel electrophoresis (1.5%; w/v).

(L) Luciferase Assay

For determination of luciferase reporter activities we used a luciferase assay kit (Promega, Mannheim, Germany) according to the manufacturers conditions. Frozen tissue samples were homogenized in reporter lysis buffer and centrifuged for 10 min at 10.000 g. Light activities were measured with a luminometer (Lumat LB9501; Berthold, Bad Wildbad, Germany). For calibration, a standard curve with luciferin (Roche, Mannheim, Germany) was generated. Protein content in tissue homogenates was determined with the Nanoorange Kit (Molecular Probes, Leiden, The Netherlands). Luciferase activities were expressed as relative light units (RLU) per mg protein.

(M) Graphics and Docking Simulation

Pictures were made with the rasmol 2.6 (Sayle et al. (1995), Trends Biochem Sci. 20:374) software and Insight2000 (Accelrys Inc., USA). Starting structures for the protein monomer and the heparin ligand were obtained from the Brookhaven Protein Data Bank (PDB entries: AAV2-protein: 1LP3 (71), heparin hexamer: 1HPN (Xie et al. (2002), Proc Natl Acad Sci U S A. 99:10405-10) and minimised with the AMBER-force field (Weiner et al. (1986), J. Comp. Chem. 7:230-252). The 3D structure of the AAV-2 capsid was performed (own software) with BIOMT information given in the PDB-file. Potentials and partial charges were derived from AMBER-force field implemented in Insight2000. Partial charges for the heparin had to be corrected for the carboxy- and the sulfate groups to fit with the net charge of −12 for the heparin hexamer. Docking on the VP trimer was performed with the program AUTODOCK 3.05 (Morris et al. (1998), J. Comp. Chem. 19:1639-1662; Goodsell et al. (1996), J. Mol. Recognit. 9:1-5) with a grid spacing of 375 nm and a rectangular grid box of 4.5 nm length.

EXAMPLE 2

Search for a Heparin Binding Motif in the AAV Capsid Protein Sequence

The search for a heparin-binding motif in the AAV-2 capsid proteins was guided by a number of theoretical considerations and previous experimental findings. Sequence comparison of AAV-2 capsid proteins with the capsid proteins of AAV-1, 4, 5- and 6 which do not bind heparin showed major differences between amino acids 443 and 602 which are all located in loop IV according to the alignment with canine parvovirus (CPV). Several published insertion and charge-to-alanine mutations affecting heparin-binding are also located in loop IV. In addition, the epitop of monoclonal antibody C37, which effectively blocks binding of AAV-2 capsids to HeLa cells maps to two amino acids stretches at the beginning and end of loop IV. Based on the assumption that AAV-2 and AAV-3 bind to different primary receptors, short amino acid stretches in the loop IV region of AAV-2 to AAV-3 (FIG. 1 mutants #1-5; Table 1) were converted and analysed these mutant viruses for capsid-, genomic-, and infectious titer. A significant reduction in infectivity was observed with mutant #4 and a modest reduction with mutant #5. Analysis of cell binding and heparin binding showed that both were reduced in mutant #4 (comprising arginine 588) but not in the neighbouring mutant #5. This made us focus on the region surrounding arginine 588, the basic residue missing in mutant #4. An extended deletion from amino acid position 587-601 (mutant #6), as well as short, partially overlapping deletions from amino acids 582-586 (mutant #7), from amino acids 584-589 (mutant #8) and from amino acids 587-590 (mutant #9) all confirmed that the region including arginines 585 and 588 is likely involved in heparin binding. The mutant viruses showed up to four log reductions in infectivity, a loss of heparin binding and a significant reduction in their ability to bind HeLa cells (Table 1).

TABLE I

| | | Infectivity[a] | | Packaging[b] | | | |
|---|---|---|---|---|---|---|---|
| Mutant | Amino acid positions | capsids/ inf. particles | Phenotype | capsids/ genomes | Phenotype | Cell binding[c] | Heparin binding[d] |
| 1 | 469-472 DIRD → SMSL | $10^3$ | wt | 21 | wt | nd | nd |
| 2 | 547-549 SEK → TTA | $10^3$ | wt | 1 | wt | nd | nd |
| 3 | 552-554 VDI → AEL | $10^3$ | wt | 26 | wt | nd | nd |
| 4 | 588-590 RQA → TAP | $2 \times 10^6$ | l.i. | 42 | wt | ± | − |
| 5 | 591, 593-594 A, AD → T, GT | $7 \times 10^4$ | r.i. | 5 | wt | + | + |
| 6 | ΔQ589-V600, L601N 587-588 NR → AC | >$10^6$ | l.i. | 5 | wt | nd | nd |
| 7 | ΔN582-G586 | $8 \times 10^5$ | l.i. | 2 | wt | − | − |
| 8 | ΔQ584-Q589 | $10^6$ | l.i. | 1 | wt | − | − |
| 9 | ΔN587-A590 | $3 \times 10^6$ | l.i. | 1 | wt | − | − |
| 10 | R447A | $5 \times 10^3$ | wt | 4 | wt | + | + |
| 11 | R459A | $2 \times 10^3$ | wt | 4 | wt | ± | + |
| 12 | R475A | $10^7$ | l.i. | 0.3 | wt | − | ± |
| 13 | R484A | $10^7$ | l.i. | 5 | wt | − | − |
| 14 | R484E | $10^6$ | l.i. | 6 | wt | − | − |
| 15 | R487A | $4 \times 10^4$ | r.i. | 7 | wt | − | − |
| 16 | R487E | $3 \times 10^7$ | l.i. | 5 | wt | − | − |
| 17 | R484E; R585E | $6 \times 10^8$ | l.i. | 7 | wt | − | − |
| 18 | K507A | $4 \times 10^3$ | wt | 27 | wt | ± | + |
| 19 | K527A | $3 \times 10^4$ | r.i. | 3 | wt | ± | ± |
| 20 | K532A | $2 \times 10^4$ | r.i. | 3 | wt | − | − |
| 21 | K544S | $1.3 \times 10^4$ | r.i. | 1 | wt | ± | + |
| 22 | K544E | $1.1 \times 10^4$ | r.i. | 1 | wt | ± | + |
| 23 | K556A | $7 \times 10^2$ | wt | 4 | wt | + | + |

TABLE I-continued

| Mutant | Amino acid positions | Infectivity[a] capsids/ inf. particles | Phenotype | Packaging[b] capsids/ genomes | Phenotype | Cell binding[c] | Heparin binding[d] |
|---|---|---|---|---|---|---|---|
| 24 | R566A | $6 \times 10^3$ | wt | 19 | wt | ± | + |
| 25 | R566E | $3 \times 10^3$ | wt | 5 | wt | ± | + |
| 26 | R585E | $1.3 \times 10^7$ | l.i. | 3 | wt | − | − |
| 27 | R585M | $9 \times 10^4$ | r.i. | 3 | wt | − | − |
| 28 | R585K | $2 \times 10^3$ | wt | 2 | wt | + | + |
| 29 | 587-588, NR → AC | $2 \times 10^6$ | l.i. | 5 | wt | ± | − |
| 30 | R588E | $2 \times 10^6$ | l.i. | 3 | wt | − | − |
| 31 | R588C | $10^6$ | l.i. | 13 | wt | ± | − |
| 32 | R588K | $10^3$ | wt | 3 | wt | + | + |
| 33 | K620A | $10^4$ | wt | 9 | wt | + | + |

[a]Infectious AAV-2 particles were quantified via dot blot replication assay as described previously (Grimm et al., (1998), Gene Ther. 9: 2745-60). The number of assembled capsids was measured using a capsid ELISA (Grimm et al., 1999). Infectivity was expressed as the ratio of the number of capsids to the number of infectious particles. The wild-type phenotype (wt) corresponds to a ratio of $\leq 10^4$; reduced infectivity (r.i.) corresponds to ratios of $>10^4$ to $<10^6$ and low infectivity (l.i.) is given by ratios of $\geq 10^6$.
[b]Packaging was measured as the ratio of capsids to viral genomes as described previously (Grimm et al. 1999). The wt phenotype indicates a packaging ratio of <50 and reduced packaging (r.p.) indicates a ratio of >50.
[c]Cell binding was measured as binding of capsids to HeLa cells using an A20 based ELISA as described in Materials and Methods. It is expressed as the percentage of binding of wt AAV-2. (+ means more than 80% binding; ± means between 40 and 80% binding and − means less than 40% binding).
[d]Heparin binding was measured as the percentage of viral particles applied to a heparin agarose column which were unbound, respectively recovered by high salt elution as determined with the A20 based capsid ELISA. (+ means more than 80% binding; ± means between 20 and 80% binding and − means less than 20% binding.

Further support for the involvement of arginine 588 in heparin-binding came from the double point mutant #29 (N587A, R588C) which also resulted in more than 1000 fold reduction in infectivity, reduced cell binding and a loss of heparin binding (Table 1). For all the mutants analysed in this report no significant effect on genome packaging was detected (Table 1). From these results, it was hypothesized that the loss of the basic charge of arginines 585 and 588 located in loop IV resulted in reduced cell binding and infectivity.

EXAMPLE 3

Involvement of Arginines 585 and 588 in Heparin Binding

Figure 1:
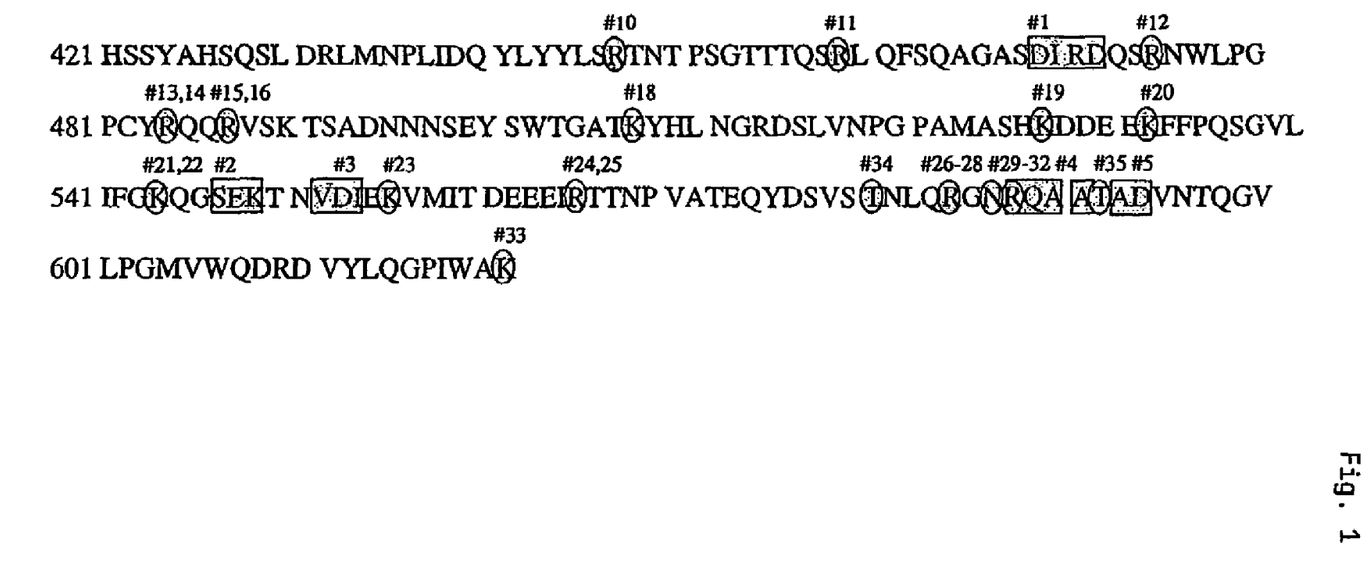
FIG. 1: Amino Acids of the AAV-2 VP Proteins Subjected to Site-Directed Mutagenesis Blockwise conversions of VP protein sequences (SEQ ID NO: 7. VP1 numbering) of AAV-2 to AAV-3 (mutants #1, #2, #3, #4 and #5) are underlayed with grey rectangles. Single mutated amino acids are marked by grey circles. Mutants are numbered according to Table 1.
Figure 2:
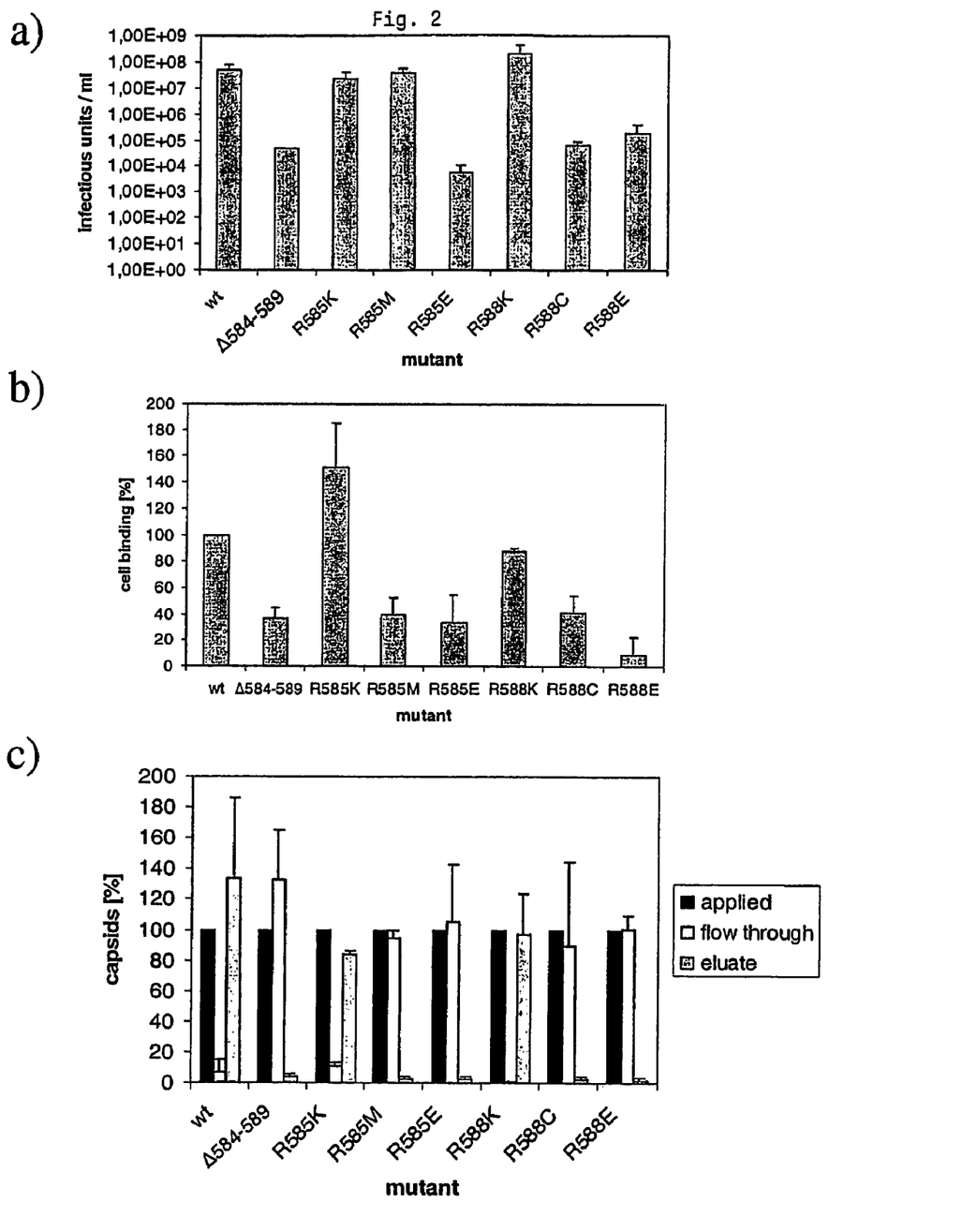

In order to substantiate these results, arginines 585 and 588 were mutated to either the acidic glutamate (E), conservatively to a basic lysine (K) or to neutral methionines or cysteines (M or C). Point mutations were compared to wt virus and mutant #8 pith respect to infectivity, cell binding and heparin binding (FIGS. 1 and 2, Table 1). Conversion of arginines 585 and 588 to glutamic acid (R585E, R588E) strongly reduced infectivity, cell binding and heparin binding similar to the deletion mutant (mutant #8). In contrast, a conservative exchange of arginine to lysine (R585K, R588K) had no negative effect on infectivity, cell binding or heparin binding. Cell-binding of R585K was in fact increased. Mutation of arginine 588 to cysteine (R588C) lowered infectivity, cell- and heparin binding, whereas mutation of arginine 585 to methionine (R585M) showed no significant effect on infectivity, although cell binding was reduced and heparin binding was lost completely. With this exception, heparin-binding correlated well with the infectivity of different mutant viruses. Taken together, these mutants support the conclusion that arginines 585 and 588 participate in heparin binding of AAV-2 capsids.

EXAMPLE 4

Arginines 484 and 487 also Contribute to Heparin Binding

Figure 3:
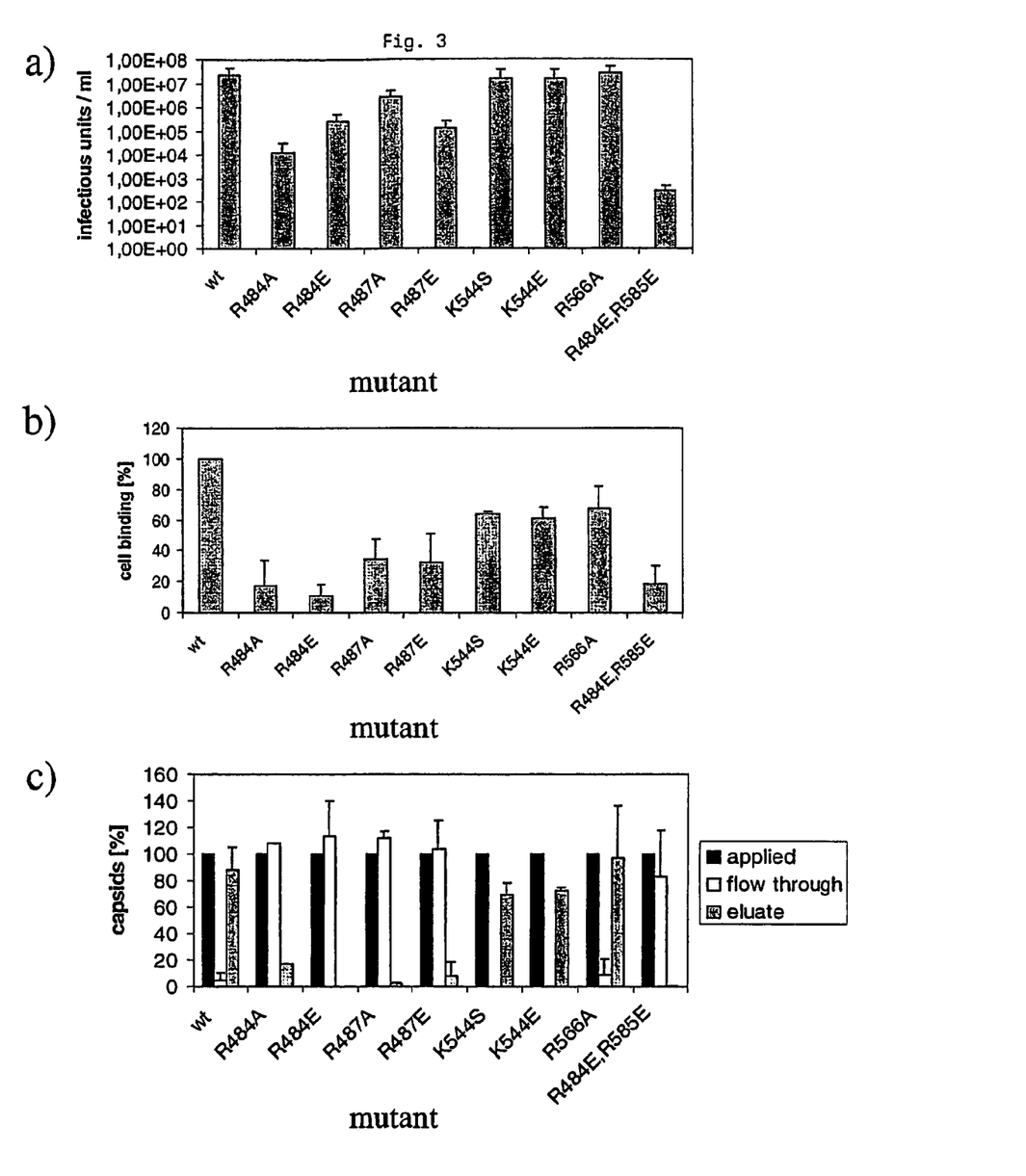

Based on the sequence alignment of AAV-2 and CPV VP3 protein and the atomic structure of the CPV capsid it was predicted that arginines 484 and 487 as well as two other basic amino acids, lysine 544 and arginine 566, could be spatially very close to arginines 585 and 588 in the folded state. Therefore, arginines 484, 487 and 566 were mutated to either alanine or glutamic acid and lysine 544 to serine or glutamic acid. All mutants were analysed for virus infectivity, packaging, cell binding and heparin binding (FIGS. 1 and 3; Table 1). Both charge-to-alanine (R484A, R487A) and basic-to-acidic mutations (R484E, R487E) of arginines 484 and 487 (mutants #13, 14, 15, 16) significantly reduced infectivity, cell binding and heparin binding. This strongly suggests that these two arginine residues form a basic cluster together with arginines 585 and 588 to strengthen heparin binding. The double mutant #17 (R484E, R585E) shows a similar loss of cell binding and heparin binding and is even more affected in its infectivity than the single mutants, further supporting our interpretation. Two mutations of lysine 544 (K544S, K544E, mutants #21, 22) showed no reduction in infectivity and a modest reduction in cell binding. Heparin binding was not significantly reduced, although recovery of the mutant virus in the high salt eluate was slightly lowered. Furthermore, mutations of arginine 566 (R566A, R566E, mutants #24, 25) were not measurably affected in infectivity and heparin binding, but again cell binding was slightly reduced. These results support the conclusion that, of the four basic amino acids predicted to be potentially located close to R585 and R588, only arginines 484 and 487 are involved in heparin-binding.

EXAMPLE 5

Further Candidate Amino Acids in Loop IV are Involved in Heparin Binding

Figure 4:
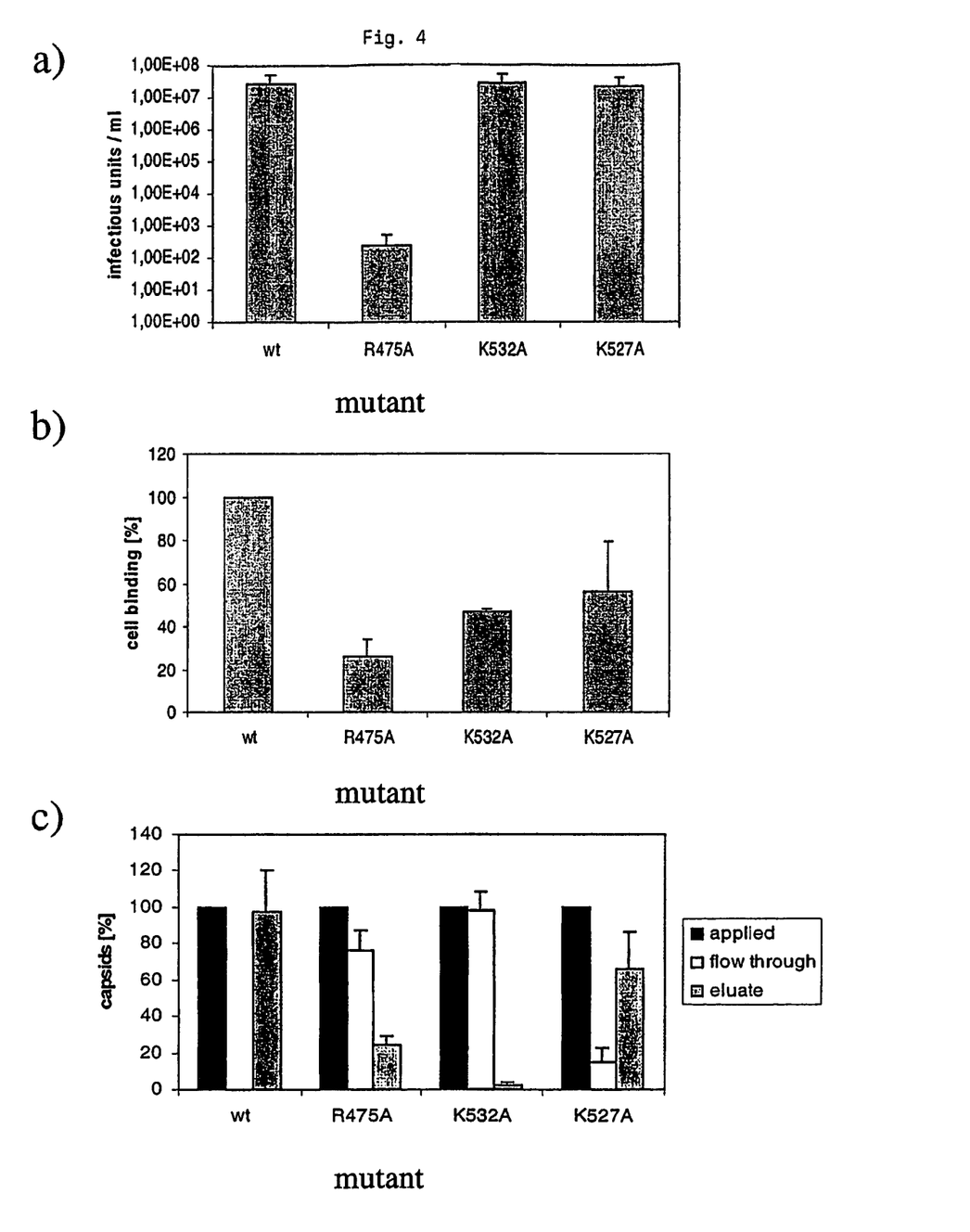

To analyse whether other basic amino acids in loop IV contribute to the basic cluster around arginines 585 and 588 upon folding and assembly, all other previously not analysed arginines and lysines between amino acid positions 446 and 620 were mutated (FIG. 1). Most residues showed no change in the parameters analysed as shown in Table 1 (mutants #10, #11, #12, #18, #19, #20, #23, #33), except mutations of arginine 475 (mutant #12) and of lysines 532 and 527 (mutants #20 and #19, respectively) (FIG. 4). Conversion of arginine 475 to alanine (R475A, mutant #12) dramatically reduced the infectivity of the mutant virus as well as cell-binding, whereas heparin binding was only partially lost. The opposite was observed for the mutation of lysine 532 (K532A, mutant #20): while heparin binding was strongly reduced and cell binding was modestly reduced, infectivity remained nearly unaffected. Mutation of lysine 527 (K527A, mutant #19) to alanine showed similar characteristics, except that heparin-binding was only moderately reduced. Based on these results, it as concluded that P475 and K532 could be part of the heparin-binding motif together with R583, R585, R487, and R484.

EXAMPLE 6

Tissue Tropism of AAV-2 Heparin-Binding Mutants In Vivo

Figure 5:
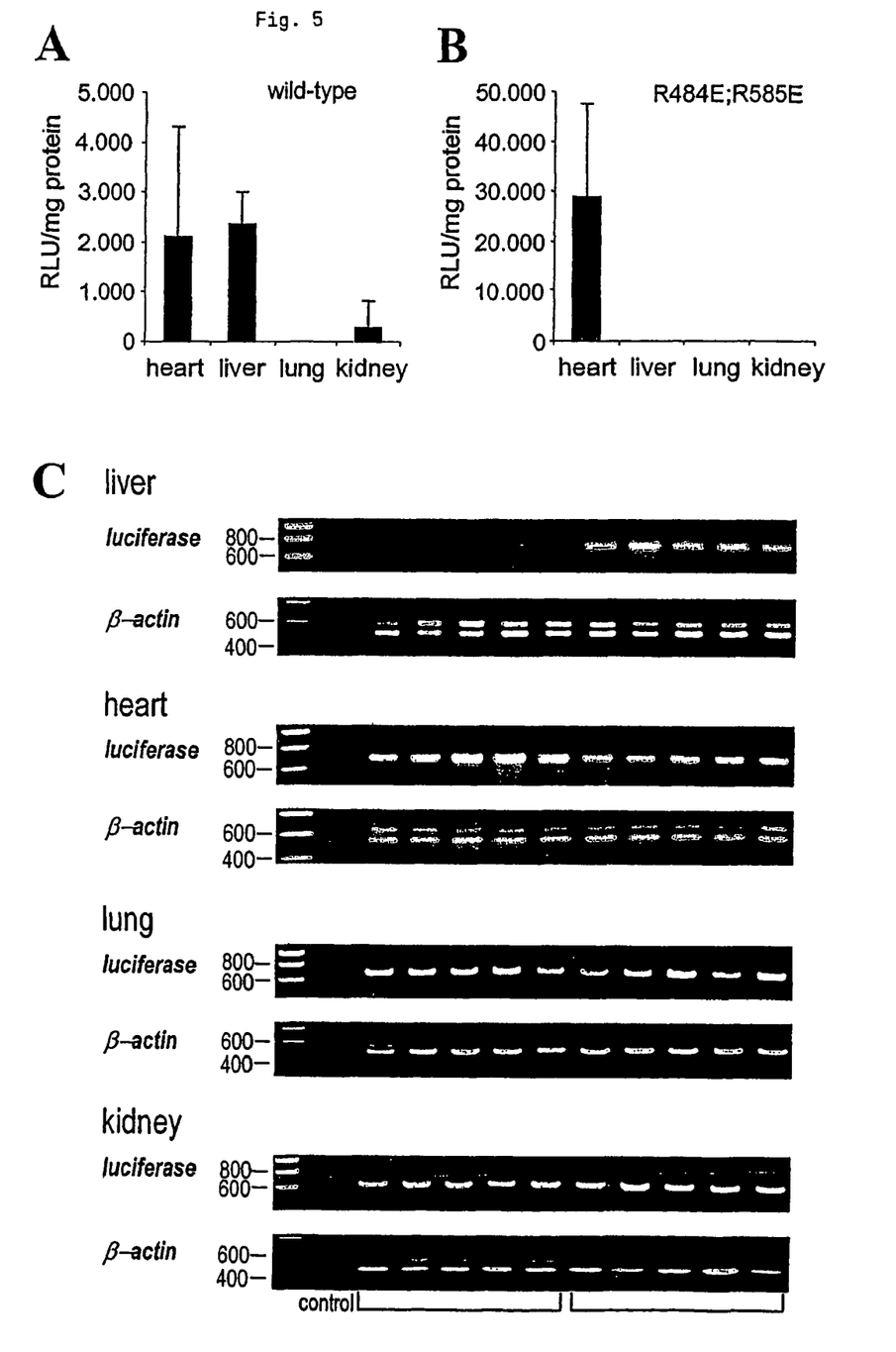
Figure 6:
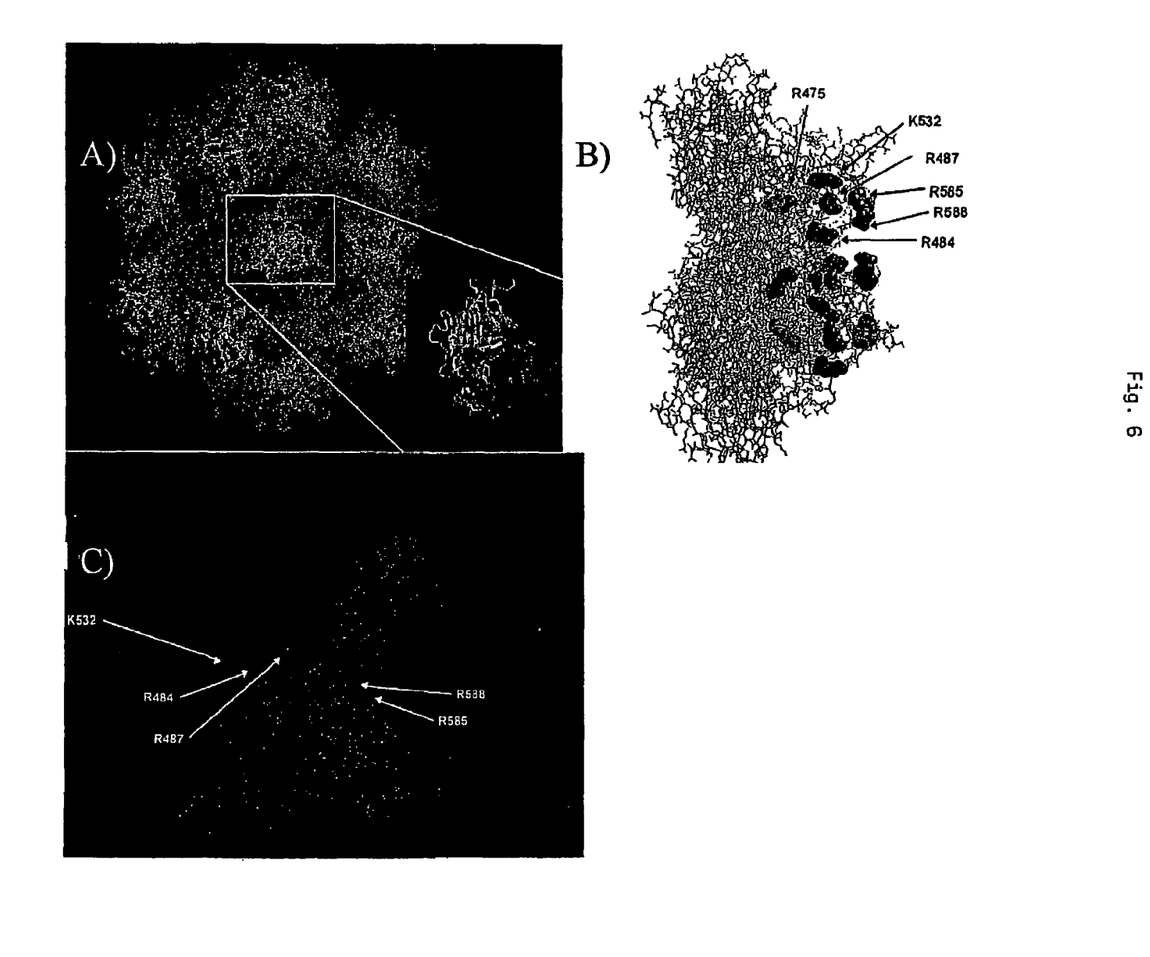
Figure 7:
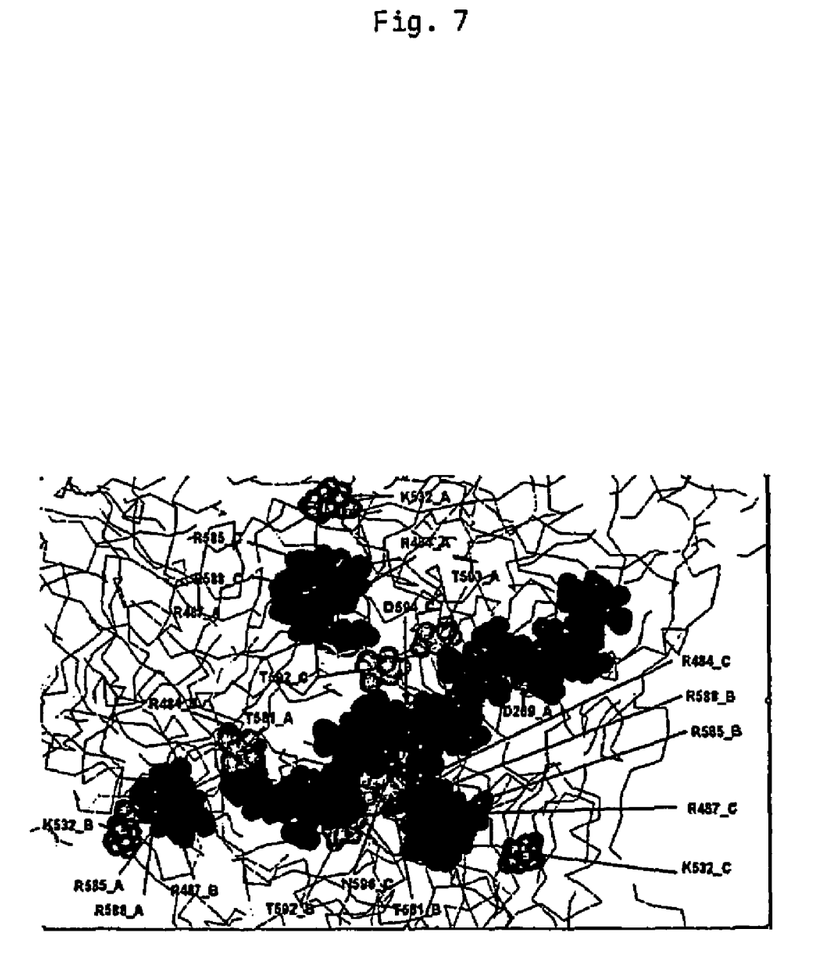

To test whether mutations in the heparin-binding motif also affect the in vivo tropism of the virus, recombinant AAV-2 (rAAV) were injected with either wt or heparin-binding mutant #17 (R484E/R585E) capsids into the tail vein of mice and analysed vector genome distribution and reporter gene expression in different tissues. The reporter gene activity of rAAV packaged into the wt capsid could be detected in the liver and heart muscle after injection of $10^{11}$ vector genomes (FIG. 5a). Luciferase activity in lung and kidney was close to background levels and could not be detected in the other tissues analysed. Reporter gene activity of the double mutated virus was not detectable in the liver, however, it was surprisingly high in the heart sample suggesting heparan-sulfate independent transduction of heart tissue in vivo (FIG. 5B). The difference in reporter gene expression between wt and double mutant vectors was confirmed by PCR analysis of vector genomes in heart and liver in several independently harvested samples (FIG. 5C). In contrary, vector genomes delivered by wt or mutant capsids could be detected by PCR in lung and kidney in similar amounts.

The invention claimed is:

1. A method of gene therapy in a heart muscle tissue of a patient, comprising delivering to the heart muscle tissue of a patient an AAV-2 vector or an AAV-2 particle having a capsid encoded by the AAV-2 vector, wherein the AAV-2 vector comprises mutations R484E and R585E according to the numbering based upon VP1 protein, which are in a heparin binding motif of a capsid protein and cause a reduced or eliminated heparin binding function, and wherein said mutations are located on different subunits of the capsid protein.

2. The method of claim 1, wherein the capsid protein is VP1, VP2, or VP3.

3. The method of claim 2, wherein the capsid protein is VP1.

4. The method of claim 1, wherein said delivering is systemic delivering.

* * * * *

SEQUENCE LISTING

<160> NUMBER OF SEQ ID NOS: 7

<210> SEQ ID NO 1
<211> LENGTH: 24
<212> TYPE: DNA
<213> ORGANISM: Artificial sequence
<220> FEATURE:
<223> OTHER INFORMATION: Chemically synthesised

<400> SEQUENCE: 1
cgttaaccca ggcatggtct gggc                                          24

<210> SEQ ID NO 2
<211> LENGTH: 27
<212> TYPE: DNA
<213> ORGANISM: Artificial sequence
<220> FEATURE:
<223> OTHER INFORMATION: Chemically synthesised

<400> SEQUENCE: 2
cccagaccat gcctgggtta acgcatg                                       27

<210> SEQ ID NO 3
<211> LENGTH: 22
<212> TYPE: DNA
<213> ORGANISM: Artificial sequence
<220> FEATURE:
<223> OTHER INFORMATION: Primer

<400> SEQUENCE: 3
gacgccaaaa acataaagaa ag                                            22

<210> SEQ ID NO 4

```
<211> LENGTH: 20
<212> TYPE: DNA
<213> ORGANISM: Artificial sequence
<220> FEATURE:
<223> OTHER INFORMATION: Primer

<400> SEQUENCE: 4
ccaaaaatag gatctctggc                                         20

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
atgtttgaga ccttcaacac                                         20

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
aacgtcacac ttcatgatgg                                         20

<210> SEQ ID NO 7
<211> LENGTH: 200
<212> TYPE: PRT
<213> ORGANISM: adeno-associated virus 2

<400> SEQUENCE: 7

His Ser Ser Tyr Ala His Ser Gln Ser Leu Asp Arg Leu Met Asn Pro
1               5                   10                  15

Leu Ile Asp Gln Tyr Leu Tyr Tyr Leu Ser Arg Thr Asn Thr Pro Ser
            20                  25                  30

Gly Thr Thr Thr Gln Ser Arg Leu Gln Phe Ser Gln Ala Gly Ala Ser
        35                  40                  45

Asp Ile Arg Asp Gln Ser Arg Asn Trp Leu Pro Gly Pro Cys Tyr Arg
    50                  55                  60

Gln Gln Arg Val Ser Lys Thr Ser Ala Asp Asn Asn Asn Ser Glu Tyr
65                  70                  75                  80

Ser Trp Thr Gly Ala Thr Lys Tyr His Leu Asn Gly Arg Asp Ser Leu
                85                  90                  95

Val Asn Pro Gly Pro Ala Met Ala Ser His Lys Asp Asp Glu Glu Lys
            100                 105                 110

Phe Phe Pro Gln Ser Gly Val Leu Ile Phe Gly Lys Gln Gly Ser Glu
        115                 120                 125

Lys Thr Asn Val Asp Ile Glu Lys Val Met Ile Thr Asp Glu Glu Glu
    130                 135                 140

Ile Arg Thr Thr Asn Pro Val Ala Thr Glu Gln Tyr Asp Ser Val Ser
145                 150                 155                 160

Thr Asn Leu Gln Arg Gly Asn Arg Gln Ala Ala Thr Ala Asp Val Asn
                165                 170                 175
```

```
-continued

Thr Gln Gly Val Leu Pro Gly Met Val Trp Gln Asp Arg Asp Val Tyr
            180                 185                 190

Leu Gln Gly Pro Ile Trp Ala Lys
        195             200
```